United States Patent
Gu et al.

(10) Patent No.: US 9,259,377 B2
(45) Date of Patent: *Feb. 16, 2016

(54) ORAL COMPOSITIONS AND METHOD FOR PRODUCING THEREOF

(75) Inventors: Ben Gu, East Brunswick, NJ (US); Mahmoud Hassan, Somerset, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/993,724

(22) PCT Filed: Dec. 13, 2010

(86) PCT No.: PCT/US2010/060088
§ 371 (c)(1),
(2), (4) Date: Jun. 13, 2013

(87) PCT Pub. No.: WO2012/082098
PCT Pub. Date: Jun. 21, 2012

(65) Prior Publication Data
US 2013/0287711 A1 Oct. 31, 2013

(51) Int. Cl.
*A61Q 11/00* (2006.01)
*A61K 8/27* (2006.01)
*A61K 8/02* (2006.01)
*A61K 8/73* (2006.01)
*A61K 8/92* (2006.01)

(52) U.S. Cl.
CPC ............. *A61K 8/0204* (2013.01); *A61K 8/0216* (2013.01); *A61K 8/27* (2013.01); *A61K 8/731* (2013.01); *A61K 8/922* (2013.01); *A61Q 11/00* (2013.01); *A61K 2800/92* (2013.01)

(58) Field of Classification Search
CPC ......... A61Q 11/00; A61K 8/731; A61K 8/27; A61K 8/25; A61K 8/21; A61K 8/0216; A61K 2800/92
USPC .................................................. 424/49, 401
See application file for complete search history.

(56) References Cited

U.S. PATENT DOCUMENTS

| | | |
|---|---|---|
| 4,713,243 A | 12/1987 | Schiraldi et al. |
| 4,894,220 A | 1/1990 | Nabi et al. |
| 5,976,507 A | 11/1999 | Wong et al. |
| 6,258,342 B1 | 7/2001 | Harcum et al. |
| 6,379,654 B1 | 4/2002 | Gebreselassie et al. |
| 6,419,903 B1 | 7/2002 | Xu et al. |
| 6,419,906 B1 | 7/2002 | Xu et al. |
| 6,514,483 B2 | 2/2003 | Xu et al. |
| 6,669,929 B1 | 12/2003 | Boyd et al. |
| 7,671,100 B2 | 3/2010 | Gaserod et al. |
| 2004/0042976 A1 | 3/2004 | Silber et al. |
| 2004/0062724 A1 | 4/2004 | Moro et al. |
| 2004/0126332 A1 | 7/2004 | Boyd et al. |
| 2004/0136924 A1 | 7/2004 | Boyd et al. |
| 2005/0019273 A1 | 1/2005 | Boyd et al. |
| 2006/0013779 A1 | 1/2006 | Dodds et al. |
| 2006/0134025 A1* | 6/2006 | Trivedi et al. ................... 424/58 |
| 2007/0154412 A1* | 7/2007 | Phillips et al. .................. 424/58 |
| 2008/0014224 A1 | 1/2008 | Boyd et al. |
| 2008/0160056 A1 | 7/2008 | Boyd et al. |

FOREIGN PATENT DOCUMENTS

JP 2009-521500 6/2009

OTHER PUBLICATIONS

Zinc Oxide Powder—USP. SoapGoods.com. Date Retrieved: Nov. 21, 2014.*
Menthol, Khimicheskaya encyclopedia [Chemical encyclopedia].—M.: "Sovetskaya entsiklopedia", Ed. by I.L. Knunyants, 1998, [online], [found on Aug. 21, 2014], found in Internet <URL: http://dic.academic.ru/dic.nsf/enc_chemistry/2565/menthol>).
Chueshov et al., "Industrial technology of medicaments", Textbook in two vol., vol. 1, Kh.:MTK-Kniga; NFAU, 2002, p. 333.
International Search Report and Written Opinion in International Application No. PCT/US10/060088.
Written Opinion in International Application No. PCT/US10/060088, mailed Dec. 12, 2012.

* cited by examiner

Primary Examiner — Frederick Krass
Assistant Examiner — Tracy Liu

(57) ABSTRACT

Methods of preparing a dentifrice comprising polymer matrix film with a low solubility flavorant therein are disclosed. The methods comprise combining a polymer matrix film that are free of a low solubility flavorant with a dentifrice base comprising a low solubility flavorant and maintaining the combined polymer matrix film with the dentifrice base comprising low solubility flavorant for an amount of time sufficient for an amount of a low solubility flavorant to transfer from the dentifrice base comprising low solubility flavorant to the polymer matrix film Products comprising low solubility flavorant-free polymer matrix film in a dentifrice base comprising low solubility flavorant are also disclosed.

12 Claims, No Drawings

ORAL COMPOSITIONS AND METHOD FOR PRODUCING THEREOF

CROSS-REFERENCE TO RELATED APPLICATIONS

This application is a National Stage Entry under 35 U.S.C. §371 of International Patent Application No. PCT/US2010/060088, filed Dec. 13, 2010, (now expired), the contents of which is hereby incorporated by reference in its entirety.

FIELD OF THE INVENTION

This invention relates to methods of making dentifrice products comprising hydratable, polymer matrix films.

BACKGROUND OF THE INVENTION

The hydratable, polymer matrix films which comprise low solubility polymer additives and are produced free of low solubility flavorants free of low solubility flavorants are combined with dentifrice base that comprises low solubility flavorant which migrates from the dentifrice base into the hydratable, polymer matrix films to form a dentifrice that comprises hydratable, polymer matrix films which include low solubility flavorants.

Liquid, gel and semi-solid oral care products which comprise hydratable, polymer matrix films containing low solubility flavorants such as menthol are known. Hydratable, polymer matrix film containing low solubility flavorants such as menthol are prepared and added into toothpaste to generate an aesthetic effect as well as to provide the benefit of a flavor and/or cooling sensation or signal. The hydratable, polymer matrix film, typically in the form of flakes or small sized pieces cut from larger manufactured films, is maintained in the product when stored. Upon use, the films typically degrade by chemical or physical disruption, thereby releasing the active or functional material into the surrounding environment. In this manner, the films provide an opportunity for localized release of a high concentration of active materials, such as for example zinc oxide, near a target surface. In addition, low solubility flavorant in the film is also released. The low solubility flavorants such as menthol in the films provide an extended flavor experience to the user compared to that which occurs when compositions in which the flavor is only in the toothpaste base are used. By including flavorants in the films, flavor may be released from films during and immediately after use, providing a flavor experience that continues after performance of the oral care process such as brushing or rinsing is completed. This extended experience can be pleasing.

Conventional methods of manufacturing hydratable, polymer matrix films that contain low solubility flavorants such as menthol comprise the step of incorporating menthol into the slurry that is then used to form the film. The low solubility flavorant is thereby dispersed throughout the slurry which is used to make the film. After the film is formed, it is typically often cut into flakes or pieces, and introduced into the toothpaste base. The step of adding relatively insoluble flavorant into the slurry used to manufacture the hydratable, polymer matrix films typically requires the use of solvents such as ethanol. When making the films, the ethanol is typically removed using heat which causes the ethanol to evaporate. The low solubility flavorants are lost as a result of evaporation of the ethanol solvent. For examples, 50% of menthol in a slurry formula is lost with the solvent when the ethanol evaporates. Moreover, the evaporated ethanol creates a safety concern in the manufacturing facility. Accordingly, introduction of low solubility flavorants into the film during its manufacture is inefficient, which leads to in additional manufacturing costs, and creates conditions which must be managed to avoid safety problems.

There is a need for improved methods of manufacturing liquid, gel and semi-solid oral care products which comprise hydrophilic films containing menthol.

BRIEF SUMMARY OF THE INVENTION

Methods of manufacturing dentifrices which comprise hydratable polymer matrix films that contain relatively water insoluble flavorants such as menthol are provided. Flavorant-free hydratable polymer matrix films which comprise hydrophobic polymer additives are produced and added to dentifrice base that contains flavorant. The flavorant from the dentifrice base is taken up in situ by the flavorant-free films. This in situ method of introducing flavorant into hydratable polymer matrix films that comprise hydrophobic additives simplifies the manufacturing process, improves safety and reduces cost.

Some aspects provide dentifrice compositions comprising low solubility flavorant-free polymer matrix film that comprises hydrophobic polymer in a dentifrice base comprising low solubility flavorant

DETAILED DESCRIPTION OF THE INVENTION

Definitions

As used herein, the term "cellulose polymer" is meant to refer to cellulose and cellulose derivatives such as cellulose ester derivative and cellulose ether derivatives.

As used herein, the term "dentifrice" includes toothpastes and gels.

As used herein, such a "pharmaceutically acceptable" or "cosmetically acceptable" component is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

As used herein, the term "polymer matrix film" is meant to refer to the product of a process wherein cellulose and derivatives thereof are used in combination with other polymers to form thin solid water hydratable film which may further comprise other components including, colloids and other particles. The polymer matrix film comprises one or more low solubility polymer additives. The polymer matrix film for example may further comprise additives such as, for example, colorants, water soluble flavorants, sweeteners, breath fresheners, whitening agents, and/or therapeutic agents such as agents that promote oral health, e.g. healthy teeth, gums and other oral tissue, and agents that prevent and treat various oral maladies. In addition, the polymer matrix film may include other film forming agents, plasticizing agents, surfactants and emulsifying agents. The polymer matrix film may be cut or otherwise divided into multiple pieces such as flakes or small strips and added to a dentifrice where they may provide aesthetic elements and/or serve as a carrier for one or more additives which may be included.

As used herein, the term "low solubility flavorant" refers to a flavor ingredient or cooling agent which is relatively insoluble in water, i.e. having the solubility generally on the order of menthol in water or less soluble. A "low solubility flavorant" must first be incorporated into a solution using a solvent such as an alcohol, particularly ethanol, in order to stably incorporate it into the slurry of hydrophilic hydratable polymer which can be used to produce hydratable polymer matrix films comprising low solubility flavorants.

As used herein, the term "low solubility flavorant-free polymer matrix film" is meant to refer to a polymer matrix film that is in the substantial absence of low solubility flavorant. Low solubility flavorant-free polymer matrix films are produced without the direct addition of low solubility flavorant, or of ingredients or solutions containing low solubility flavorant into the slurry used to make the low solubility flavorant-free polymer matrix film.

As used herein, the term "substantial absence" is meant to refer to a film that has a low solubility flavorant content on film formation of less than 0.5%.

As used herein, the term "low solubility polymer additive" refers to a generally water insoluble polymer in which a low solubility flavorant is soluble. When a low solubility polymer additive is present in a polymer matrix film, the film has a greater capacity to undergo reverse migration of low solubility flavorant from a dentifrice base comprising flavorant to the polymer matrix film that comprises the copolymer additive. In addition or alternatively, when a low solubility polymer additive is present in a polymer matrix film, the film has a greater capacity to maintain a high concentration of when the polymer matrix comprising polymer is present in a dentifrice base comprising low solubility flavorant compared to concentration levels of when the polymer matrix comprising polymer is present in a dentifrice base comprising low solubility flavorant in a polymer matrix film that is free of polymer when such film is maintained in a dentifrice base comprising flavorant.

As used herein, the term "transferring" refers to migration, moving or transporting flavorant from the dentifrice base into the film. Passive transfer typically does not require an external agent (e.g., mechanical force, chemical and/or thermal energy) to achieve movement of the low solubility flavorant. Passive transfer typically encompasses mass transport phenomena including diffusion, where the flavorant molecules are physically transported across a concentration gradient to approach then thermodynamic equilibrium. Further, passive transfer may include electrochemical interaction, absorption, adsorption, and/or wicking movement of the flavorant into the film, where application of an external agent is not required to achieve sufficient movement of the flavorant into the film. Active transport is generally not required. However, in some embodiments, ingredients may be provided to drive equilibrium to promote transfer of flavorant from the dentifrice base to the polymer matrix film.

Throughout the present disclosure, ranges are used as shorthand for describing each and every value that is within the range. Any value within the range can be selected as the terminus of the range. Furthermore, all references cited throughout the disclosure are expressly incorporated by reference in their entireties. As used herein, all references to concentration of ingredients are on a weight basis, unless otherwise indicated.

Unless otherwise specified, all percentages and amounts expressed herein and elsewhere in the specification should be understood to refer to percentages by weight. The amounts given are based on the active weight of the material.

Overview

Aspects of the present invention relate to methods of making a gel and semi-solid oral care products such as toothpaste which comprise polymer matrix films that contain low solubility flavorant such as menthol. The polymer matrix films comprise one or more low solubility polymer additives. Some of the methods comprise producing a low solubility flavorant-free hydratable polymer matrix and eliminating the use of alcohol that is required when incorporating low solubility flavorant into the polymer slurry used to make polymer matrix films. The low solubility flavorant-free hydratable polymer matrix film is combined with a dentifrice base that comprises a low solubility flavorant and the low solubility flavorant transfers from the dentifrice base into the polymer matrix film. Thus, after being combined with the dentifrice base that comprises low solubility flavorant, flavorant becomes incorporated into what was formerly low solubility flavorant-free polymer matrix film and the resulting combination includes polymer matrix films that comprise low solubility flavorant dispersed in dentifrice base. The low solubility flavorant is transferred from dentifrice base into the polymer matrix film such that the polymer matrix film contains flavorant at a concentration nearly equal to, equal to or greater than the concentration of flavorant in the base. The low solubility polymer additive serves to promote the transfer of low solubility flavorant into the polymer matrix film and to maintain the concentration of the low solubility flavorant in the polymer matrix film after transfer has occurred. The transferred flavorant is stable during storage of the composition.

In various embodiments, the invention provides methods which eliminate a step performed in the conventional process of making dentifrice products that comprise polymer matrix films which include low solubility flavorant such as menthol. The step that may be eliminated is a step involving making a flavorant solution having low solubility flavorant in a solvent such as ethanol or another alcohol or solvent system. In the conventional process, the flavorant solution is included in the slurry that is processed into the polymer matrix film. The alcohol used to incorporate the low solubility flavorant into the slurry is removed by evaporation. By removing the alcohol in this way, low solubility flavorant is lost from the slurry with the alcohol in the evaporation process, resulting in the actual amount of low solubility flavorant in the polymer matrix films to be less than the amount of low solubility flavorant added to the slurry. This loss increases costs and the need for larger amounts of low solubility flavorant. Moreover, steps must be taken to prevent any hazards that may arise in the manufacturing process due to evaporated alcohol in the manufacturing facility.

Thus, in the conventional method, the polymer matrix films contain low solubility flavorant prior to their addition to the dentifrice base. The preparation and use of an alcohol-based solution is eliminated by producing low solubility flavorant-free polymer matrix films and combining them into dentifrice base that comprises a solubility flavorant. The low solubility flavorant-free polymer matrix films comprise a low solubility polymer component. When these low solubility flavorant-free polymer matrix films are included in a dentifrice base that comprises low solubility flavorant, the flavorant migrates from the base into the polymer matrix films. The resulting product is a dentifrice having hydratable, polymer matrix films which comprise low solubility flavorant. The modification of the conventional process reduces costs of materials and eliminates potential safety issues that exist when using ethanol solutions.

Polymer Matrix Films

Polymer matrix films provided herein comprise one or more species of water soluble polymers such as cellulose polymers, other polysaccharides and other polymers which are generally hydrophilic. Polymer matrix films may also comprise numerous other ingredients.

Typically, polymer matrix films comprise polymers present in an amount between 30% and 90% of the polymer matrix film's dry weight. The polymers may be present in an amount of between 40% and 80% of the polymer matrix film's dry weight. Some embodiments comprise polymers in an amount between 40% and 70% of the polymer matrix film's dry weight. Some embodiments comprise polymers an amount between 40% and 60% of the polymer matrix film's dry weight. Some embodiments comprise polymers an amount between 40% and 50% of the polymer matrix film's dry weight. Some embodiments comprise polymers in an amount between 50% and 80% of the polymer matrix film's dry weight. Some embodiments comprise polymers an amount between 60% and 80% of the polymer matrix film's dry weight. Some embodiments comprise polymers an amount between 65% and 75% of the polymer matrix film's dry weight.

Films useful for the present invention may be rigid or flexible, comprising any of a variety of materials, including film forming materials. In some embodiments, the film comprises at least one film-forming material, preferably comprising a polymer. Useful polymers include hydrophilic polymers, i.e. polymers soluble in a solvent, such as water. A water-soluble polymer that dissolves during exposure to water and application of physical force during use (such as during tooth brushing or scrubbing with a brush or pad) is desirable. Where the polymer does not fully break down during use, it may be a water-repellant polymer or an aqueous-stable hydrophilic polymer such as certain types of cellulose, e.g., paper. Examples of useful polymers are described in U.S. Pat. No. 4,713,243 to Schiraldi et al., U.S. Pat. Nos. 6,419,903, 6,419,906, 6,514,483 all to Xu, and U.S. Pat. No. 6,669,929 to Boyd et al.; United States Patent Publication Nos. 2004/0126332, 2004/0136924, and 2004/0042976 all to Boyd et al., and 2004/0062724 to Moro et al.

The polymer matrix film is hydratable, comprises a low solubility polymer additive and is free of low solubility flavorants. Additionally, the formulation of the polymer matrix films may be selected to affect release of active ingredient such as the amount released proportional to how vigorously or how long the composition is used, e.g., by brushing, scrubbing, or other mechanical action during use of the aqueous composition. The formulation of the polymer matrix films may be selected to produce an overall delayed and/or extended release of flavorant, thereby providing a flavor experience following product use.

Polymers

Cellulose polymers are well known as is their use in water hydratable polymer matrix films. Cellulose polymers may be water soluble or water insoluble. Examples of cellulose derivatives include, but are not limited to: hydroxyalkyl methyl celluloses such as hydroxypropyl methyl cellulose, hydroxybutyl methyl cellulose, hydroxyethyl methyl cellulose, hydroxymethyl methyl cellulose and hydroxyethylpropyl methyl cellulose; carboxyalkyl methylcelluloses such as carboxypropyl methyl cellulose, carboxybutyl methyl cellulose, carboxyethyl methyl cellulose, carboxymethyl methyl cellulose and carboxyethylpropyl methyl cellulose; hydroxyalkyl celluloses such as hydroxypropyl cellulose, hydroxybutyl cellulose, hydroxyethyl cellulose, hydroxymethyl cellulose and hydroxyethylpropyl cellulose; alkyl celluloses such as propyl cellulose, butyl cellulose, ethyl cellulose (Ethocel™), methyl cellulose (Methocel™); and carboxyalkyl celluloses such as carboxypropyl cellulose, carboxybutyl cellulose, carboxyethyl cellulose, carboxymethyl cellulose and carboxyethylpropyl cellulose. Cellulose and cellulose ether derivative polymers may be of any length or combination of lengths. Moreover, the ranges of percent of substitutions may vary to ranges up to 100%. In molecules comprising two or more different substituting groups, the percentage substitution for each group is independent of the other groups.

The ratio of water soluble to low solubility cellulose polymers ranges from 10:1 to 5.5:2 for particularly useful polymer matrix films that provide good transfer characteristics of low solubility flavorants from base to polymer matrix film while providing good disintegration characteristics in aqueous liquid solutions. In some embodiments, the ratio of water soluble cellulose polymer to low solubility polymer that is incorporated in the polymer matrix film is 70:7, 69:9, 68:9, 67:10, 66:11, 65:12, 64:13, 63:14, 62:15, 61:16, 60:17, 59:18, 58:19, 57:20, 56:21. In some embodiments, the ratio of water soluble cellulose polymer to low solubility polymer that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1. The cumulative amount of water soluble cellulose derivative and low solubility polymer that is incorporated in the polymer matrix film is typically 40%-90%, in some embodiments 50% to 80%. In some embodiments, the cumulative amount of water soluble cellulose derivative and low solubility polymer incorporated in the polymer matrix film is 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% or 90%. In some embodiments, the cumulative amount of water soluble cellulose derivative and low solubility polymer incorporated in the polymer matrix film is 75% to 80%, and the ratio of water soluble cellulose polymer to low solubility polymer that is incorporated in the polymer matrix film is 70:7, 69:9, 68:9, 67:10, 66:11, 65:12, 64:13, 63:14, 62:15, 61:16, 60:17, 59:18, 58:19, 57:20, 56:21. In some embodiments, the cumulative amount of water soluble cellulose derivative and low solubility polymer incorporated in the polymer matrix film is 75% to 80%, and the ratio of water soluble cellulose polymer to low solubility polymer that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1. In some embodiments, the cumulative amount of water soluble cellulose derivative and low solubility polymer incorporated in the polymer matrix film is 77%, and the ratio of water soluble cellulose polymer to low solubility polymer that is incorporated in the polymer matrix film is 70:7, 69:9, 68:9, 67:10, 66:11, 65:12, 64:13, 63:14, 62:15, 61:16, 60:17, 59:18, 58:19, 57:20, 56:21. In some embodiments, In some embodiments, the cumulative amount of water soluble cellulose derivative and low solubility polymer incorporated in the polymer matrix film is 77%, 78% or 79% and the ratio of water soluble cellulose polymer to low solubility polymer that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1.

In some embodiments, the amount of low soluble polymer by weight is 21% or less. In some embodiments, the amount of low soluble polymer by weight is 11% or more. In some embodiments, the amount of low soluble polymer by weight is 12%, 13%, 14%, 15%, 16%, 17%, 18%, 19%, or 20%.

In some embodiments, the amount of water soluble cellulose polymer by weight is 66% or less. In some embodiments, the amount of water soluble cellulose polymer by weight is 56 or more. In some embodiments, the amount of water soluble cellulose polymer by weight is 65%, 64%, 63%, 62%, 61%, 60%, 59%, 58%, or 57%.

One or more species of water soluble polymers and one or more species of water insoluble polymers may be used to manufacture the polymer matrix films provided herein. An example of water insoluble cellulose polymers is ethyl cellulose. Typically, the ethyl cellulose used is from the family of ethyl cellulose products are available commercially from the Dow Chemical Company under the trade designation Ethocel™. An example of water soluble cellulose polymers is hydroxypropyl methyl cellulose (HPMC). Typically, HPMC used is from the family of HPMC and methyl cellulose (MC) products are available commercially from the Dow Chemical Company under the trade designation Methocel™. The ratio of HPMC and ethyl cellulose ranges from 10:1 to 5.5:2 for particularly useful polymer matrix films that provide good transfer characteristics of low solubility flavorants from base to polymer matrix film while providing good disintegration characteristics in aqueous liquid solutions. In some embodiments, the ratio of Methocel™ (for example Methocel™ E5) to Ethocel™ (for example Ethocel™ S4) that is incorporated in the polymer matrix film is 70:7, 69:9, 68:9, 67:10, 66:11, 65:12, 64:13, 63:14, 62:15, 61:16, 60:17, 59:18, 58:19, 57:20, 56:21. In some embodiments, the ratio of Methocel™ (for example Methocel™ E5) to Ethocel™ (for example Ethocel™ S4) that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1. In some embodiments, the cumulative amount of Methocel™ (for example Methocel™ E5) to Ethocel™ (for example Ethocel™ S4) incorporated in the polymer matrix film is 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% or 90% by weight. These amounts and ratios are particularly useful polymer matrix films that provide good transfer characteristics of low solubility flavorants from base to polymer matrix film while providing good disintegration characteristics in aqueous liquid solutions. In some embodiments, the cumulative amount of HPMC, such as Methocel™ (for example Methocel™ E5), and ethyl cellulose, such as Ethocel™ (for example Ethocel™ S4), incorporated in the polymer matrix film is 75% to 80%, and the ratio of HPMC, such as Methocel™ (for example Methocel™ E5), to ethyl cellulose, such as Ethocel™ (for example Ethocel™ S4), that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1. In some embodiments, the cumulative amount of HPMC, such as Methocel™ (for example Methocel™ E5), and ethyl cellulose, such as Ethocel™ (for example Ethocel™ S4), incorporated in the polymer matrix film is 77%, and the ratio of HPMC, such as Methocel™ (for example Methocel™ E5), to ethyl cellulose, such as Ethocel™ (for example Ethocel™ S4), that is incorporated in the polymer matrix film is 70:7, 69:9, 68:9, 67:10, 66:11, 65:12, 64:13, 63:14, 62:15, 61:16, 60:17, 59:18, 58:19, 57:20, 56:21. In some embodiments, In some embodiments, the cumulative amount of HPMC, such as Methocel™ (for example Methocel™ E5), and ethyl cellulose, such as Ethocel™ (for example Ethocel™ S4), incorporated in the polymer matrix film is 77%, 78% or 79% and the ratio of HPMC, such as Methocel™ (for example Methocel™ E5), to ethyl cellulose, such as Ethocel™ (for example Ethocel™ S4), that is incorporated in the polymer matrix film is 10:1, 9.75:1, 9.5:1, 9.25:1, 9:1, 8.75:1, 8.5:1, 8.25:1, 8:1, 7.75:1, 7.5:1, 7.25:1, 7:1, 6.75:1, 6.5:1, 6.25:1, 6:1, 5.75:1, 5.5:1, 5.25:1, 5:1, 4.75:1, 4.5:1, 4.25:1, 4:1, 3.75:1, 3.5:1, 3.25:1, 3:1 or 2.75:1.

In some embodiments, the amount of Ethocel™ (for example Ethocel™ S4) by weight is 21% or less. In some embodiments, the amount of Ethocel™ (for example Ethocel™ S4) by weight is 11% or more. In some embodiments, the amount of Ethocel™ (for example Ethocel™ S4) by weight is 12%, 13%, 14%, 15%, 16%, 17%, 18%, 19%, or 20%.

In some embodiments, the amount of Methocel™ (for example Methocel™ E5) by weight is 66% or less. In some embodiments, the amount of Methocel™ (for example Methocel™ E5) by weight is 56 or more. In some embodiments, the amount of Methocel™ (for example Methocel™ E5) by weight is 65%, 64%, 63%, 62%, 61%, 60%, 59%, 58%, or 57%.

Colloids and Colloidal Particles

In some embodiments, polymer matrix films comprise colloids. The colloid may present in an amount between 10% and 60% of the polymer matrix film's dry weight. The colloid may present in an amount between 20% and 50% of the polymer matrix film's dry weight. The colloid may present in an amount between 30% and 50% of the polymer matrix film's dry weight. The colloid may present in an amount between 40% and 50% of the polymer matrix film's dry weight.

Colloids and colloidal particles can be used to stabilize polymer matrices and fine tune its rigidity in order to provide films that are flexible enough to process, yet physically and cosmetically stable. As films are optimized, it is important to identify the parameters that will deliver optimal film performance. These parameters can be determined by quantifying the properties of the film at both the slurry stage and the dry film stage. At the slurry stage, the interactions between the polymers and the other film ingredients, including colloidal particles, form the structure of the film matrix. The viscoelastic properties of the slurry, such as the viscosity and the structural parameter (G'), enable the characterization of structural arrangement within the slurry and the processability of the same. Following processing and drying of the slurry, the bulk film is formed, setting the polymer matrix. Mechanical properties, such as the glass transition temperature, the tensile strength, and the dissolution time can be used to determine the stability of the film. By balancing the microstructural properties, such as the polymer interactions, with the macrostructural properties of the film, such as the mechanical properties, film can be made more cosmetically stable and can be better utilized as a delivery platform for various actives.

In some embodiments, colloidal particles are present in the film in the range of 40-50% dry weight.

Water-insoluble colloidal metal compounds of multivalent metals are preferred. Representative metal oxides suitable for use in the compositions described herein include silicon oxide (SiO2), molybdenum oxide ($Mo_2O_3$), aluminum oxide ($Al_2O_3$), titanium oxide (TiO), zirconium oxide ($ZrO_2$) and zinc oxide (ZnO).

Particle size may be 1 to 1000 nm. Preferably the particles have an average particle size of 1 μm to 850 nm, 50 μm to 150 nm, 15 nm to 500 nm, 30 nm to 250 nm and/or 5 μm to 100 nm.

In some embodiments, the particles are non-aggregated. By non-aggregated it is meant that the particles are not massed into a cluster having a size greater than 1 micron, preferably greater than 950 nm or 850 nm. However, particles may be mixed with aggregated particles and other colloidal particles that have an average particle size of greater than 1 micron if desired. In some embodiments, more than 80% of particles are non-aggregated. In some embodiments, more than 90% of particles are non-aggregated.

In some embodiments, colloidal particles are provided in the dentifrice base. In some embodiments, colloidal particles are provided in the dentifrice base and the polymer matrix film. In some embodiments, colloidal particles are provided in the dentifrice base but not the polymer matrix film.

Preparation of Film Matrix

In preparing the film matrix, the water soluble polymers, low solubility polymer and any of the optional ingredients, including for example, such as those set forth below as "Other Components", are dissolved or otherwise mixed into a compatible solvent to form a film forming composition. The film forming composition may contain no flavorant and no flavor solvent. The film forming composition is cast on a releasable carrier and dried to form a sheet of film matrix material. In some embodiments, the carrier material has a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

The slurries that are precursors to the films may be characterized using rheology. In some embodiments, the viscoelastic properties of the film slurry, as quantified using $G'$ as an indicator of the structural character of the polymer-particle network, may be 220-560. In some embodiments $G'$ is 223-550. In some embodiments, the structure of the polymer-particle matrix is not weak and the slurry is not essentially liquid-like. In some embodiments, the structure of the polymer-particle matrix is not very rigid thereby not leading to the formation of a very brittle film. In some embodiments, the viscosity profile as a function of shear rate is quantified as a measure of flowability and processability the slurries. In some embodiments, the viscosity profiles are not a semi-dilute solution. The viscosity in poise is measured at 0.3 s-1. In some embodiments, the viscosity (taken at 0.3 s-1) for the various slurries is 175-475. In some embodiments, the viscosity (taken at 0.3 s-1) for the various slurries is 183-450.

The films of the present invention preferably have a substantially lamellar structure. A "lamellar" structure has a size in one or two dimensions (e.g., x- or y-dimensions) that is substantially greater than the thickness of the structure in a third dimension (e.g., the z-dimension), and generally includes substantially planar, layered, or lamelliform shapes, for example. In one embodiment, the lamellar structure is substantially planar, having a size in both the x- and y-dimensions that is substantially greater than the z-dimension. In other embodiments, the lamellar structure is non-planar. In one embodiment, a film comprises a substantially continuous surface that can appear as a substantially flat surface, although in some embodiments the film may be deformed. In such embodiments, the film can have any of a number of shapes, including having a smooth, curved surface. Further, the term "film" encompasses both a single structure as well as a plurality of film fragments. In certain embodiments, the film comprises a plurality of fragments independently having a thickness of 0.1 mils to 10 mils, preferably 0.5 mils to 9 mils, and more preferably 1.2 mils to 3 mils. In some embodiments, the film thickness range is 2 to 3 microns. A preferred length of the fragments is at least 0.2 mm.

The dried film is then processed for inclusion in the dentifrice. The film may be cut or punched into small strips or squares. In various embodiments, the film comprises a plurality of fragments or pieces. Such fragments may be of any of a variety of shapes or forms, including semi-solid or solid discrete portions, fragments, particles, flakes, or mixtures thereof. In various embodiments, the film fragments have a recognizable shape. In some embodiments, a film fragment comprises a nonrandom shape. Such shapes include simple geometric shapes such as polygons, elliptical shapes, triangles, quadrilaterals (such as a square, a rectangle, a rhombus), pentagons, hexagons, ovals, circles, or shapes that are representative of figures, animate or inanimate objects, such as stars, hearts, gems, flowers, trees, shamrocks, letters, numbers, animals, characters, diamonds, circles and the like. The dried film may be cut or punched into shaped flakes having a particle size of 0.01 to 0.50 inches preferably 0.08 to 0.25 inches. Additional stability can be provided to the shapes formed from the dried film, by applying to the film, before shaping into flakes or small strips, a protective barrier overcoat such as a food grade shellac or ethyl cellulose.

Further, the plurality of film fragments may have different compositions, for example having a first plurality of film fragments comprising a first color, and a second plurality of film fragments comprising a second color, where the first and second colors are different from each other. Any permutation of different compositions is contemplated, for example, any number of different active ingredients in the compositions or different film compositions.

Base Dentifrice Composition

Examples of suitable carriers for oral care compositions are disclosed in U.S. Pat. No. 6,669,929 to Boyd et al., U.S. Pat. No. 6,379,654 to Gebreselassie et al., and U.S. Pat. No. 4,894,220 to Nabi et al.

The dentifrice (toothpaste or gel) is typically water based. As recognized by one of skill in the art, the dentifrice optionally include other materials and mixtures thereof, including for example, such as those set forth below as "Other Components". It is understood that while general attributes of each of the above categories of materials may differ; there may be some common attributes, and any given material may serve multiple purposes within two or more of such categories of materials.

In the preparation of the base dentifrice in accordance with the present invention there is utilized an orally acceptable vehicle, including a water-phase with humectants. Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners. One or more humectants are optionally present in a total amount of 1% to 50%, for example 2% to 25% or 5% to 15%. Humectants are present typically in amount of 5 to 10% by weight in water, typically, 30 to 80% by weight of the dentifrice, more typically 50 to 70% by weight.

The base dentifrice may also contain an inorganic or a natural or synthetic thickener or gelling agent. Optionally, one or more thickening agents are optionally present in a total amount of 0.01% to 15%, in some embodiments 0.1% to 10%, in some embodiments 0.10 to 5% by weight, in some embodiments 0.2% to 5% by weight and in some embodiments 0.2 to 1% by weight. These proportions of thickeners in the dentifrice compositions of the present invention in which the film flakes of the present invention are suspended are sufficient to form an extrudable, shape-retaining product which can be squeezed from a tube onto a toothbrush and will not fall between the bristles of the brush but rather, will substantially maintain its shape thereon. Suitable thickeners or gelling agents useful in the practice of the present invention include inorganic thickening silicas such as amorphous silicas available from Huber Corporation under the trade designation Zeodent 165, Irish moss, iota-carrageenan, polyvinylpyrrolidone, carboxyvinyl polymers, cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica and mixtures thereof.

In various embodiments, an dentifrice composition is provided within a single component or phase. In other embodiments, the composition includes both a first and a second component that are separately maintained. Maintaining the components separately requires only that the components are maintained in such a way as to substantially prevent the interaction of one component of the composition with another component of the composition. Typically, a dual component oral care composition is employed where there are one or more incompatible ingredients included in the composition. For example, if the dentifrice comprises two incompatible active ingredients, it is advantageous to maintain them separately. While the films comprising active ingredients generally provide a degree of separation, there may be some migration of active from the film into the carrier, and vice versa, and as such, in some cases it may desirable to provide an entirely separate phase. The separation of components can be accomplished through any means known or to be discovered in the art and includes chemical, physical, and mechanical means of separation of any combination of these. For example, the first and second incompatible components may be combined but certain components are separately maintained by wrapping or encapsulating one or both in a protective film, coating, capsule, micelle, etc.

The low solubility flavorant is present in the dentifrice base in concentrations of 0.025-10% by weight. Typically, low solubility flavorant is present in the base at a concentration of 0.05 to 7.5% based on the total weight. In some embodiments, low solubility flavorant is present in a concentration of 0.1 to 5% by weight, in some embodiments, 0.5 to 2.5% by weight, in some embodiments, 0.75 to 2% by weight, in some embodiments, 1.0 to 1.5% by weight.

Typically, to prepare the dentifrice base, water, humectants, e.g. glycerin, sorbitol polyethylene glycol are dispersed in a conventional mixer until the mixture becomes a homogeneous gel phase. Into the gel phase are added other ingredients and mixed until a homogeneous phase is obtained. Thereafter the thickener, any flavor and surfactant ingredients are added and the ingredients mixed at high speed until vacuum of 20 to 100 mmHg.

In some embodiments, the dentifrice base comprises one or more other components selected from the group consisting of: polyethylene glycol, CMC, sodium saccharin, sodium fluoride, sorbitol (70% solution), purified water, colorant, silica zeodent, cocoamidopropyl betaine and sodium lauryl sulfate.

Low Solubility Flavorants

Menthol is contemplated to be the preferred low solubility flavorant. In addition to menthol, other low solubility flavor ingredients or cooling agents, natural or synthetic, may be incorporated into polymer matrix films using in-situ flavoring of films produced free of low solubility flavorants by adding the films produced free of low solubility flavorants into any toothpaste base which comprises the low solubility flavorants.

Flavor agents are known, such as natural and artificial flavors. These flavorants may be chosen from synthetic flavor oils and flavoring aromatics, and/or oils, oleo resins and extracts derived from plants, leaves, flowers, fruits and so forth, and combinations thereof. In addition to menthol, representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. To be considered low solubility flavorants, the flavorants may be hydrophobic, insoluble or must be sufficiently insoluble in water so that they must be solubilized in a solvent such as ethanol or another alcohol in order to incorporate them into a slurry that can be used to produce a polymer film matrix at a practical level for use as a flavorant.

The low solubility flavorants may be present in the dentifrice base in an amount sufficient for an effective amount to be transferred from the base into the low solubility flavorant-free poly matrix films within a time period typically 1 hour to 7 days after the introduction of such films into the base.

Other Components

Additional components may also be included in the dentifrice base and/or the polymer matrix films. In some embodiments, one or more additional components are provided in both the dentifrice base and the polymer matrix film. In some embodiments, one or more additional components are provided are provided in the dentifrice base but not the polymer matrix film. In some embodiments, one or more additional components are provided in the polymer matrix film but not in the dentifrice base.

Preferably, the polymer matrix film and/or the dentifrice base optionally comprises one or more of the following additional components: surface active agents, bulking agents, viscosity modifiers, surfactants, thickeners, humectants, diluents, fillers (in addition to those described above), pH modifying agents, plasticizers, fillers, waxes, texture modifiers, oils, flavoring and/or sweetening agents, colorants, dyes, whitening agents, breath freshening agents, abrasives, polishing agents, preservatives, solvents, and mixtures thereof. In embodiments prophylactic and therapeutic agents such as: cetylpyridinium chloride, chlorhexidene, fluoride ion sources, stannous ion sources, tartar control (anticalculus) agents, antimicrobial (e.g., antibacterial) agents, antioxidants, saliva stimulating agents, antiplaque (e.g., plaque disrupting) agents, anti-inflammatory agents, H2 antagonists, desensitizing agents, nutrients, proteins and combinations and mixtures thereof. It is understood that while general attributes of each of the above categories of materials may differ; there may be some common attributes, and any given material may serve multiple purposes within two or more categories of materials.

Polymer matrix films may comprise hydrophobic/lipophilic additives include compounds which can be incorporated into the polymer matrix films, particularly during manufacture and which, when in incorporated as part of a polymer matrix film, can serve to attract low solubility flavorants from the dentifrice base and concentrate them to the polymer matrix film. Illustrative examples of hydrophobic/lipophilic additives suited for inclusion into the composition include, fats and oil including but not limited to, petrolatum, silicone oil, beeswax, hydrogenated soybean oil, sweet almond oil, peanut oil, avocado oil, borage oil, palmitic acid, cacao butter, carnauba wax, castor oil, coconut oil, evening primrose oil, glycerin, glyceryl stearate, jojoba oil, camphor, kaolin, lanolin, cod liver oil, linseed oil, corn oil, olive oil, palm oil, paraffin, squalane, rapeseed oil, rose oil, safflower oil, sesame oil, shea butter, dimethicone silicone oil, tall oil, wheat germ oil, sunflower oil, trimethylsiloxysilicate, alkyldimethylsilyl solypropylsesquioxane, dimethiconol, trimethylsiloxysilicate, polyether-modified silicone, cross-linked polymers, polypropylsilsesquioxane, dimethicone polymers, dimethicone crosspolymer, dimethicone/vinyl dimethicone cross polymers, other fats and oils, and combinations thereof.

Dentifrice Composition comprising Dentifrice Base and Polymer Matrix Films

The film flakes and strips made from the low solubility flavorant-free polymer matrix film that comprise a low solubility polymer are incorporated in the base dentifrice of the present invention, preferably at a concentration of 0.05 to 1.0% by weight and preferably 0.1 to 0.5% by weight. The film flakes or strips are generally added to the dentifrice base as a last step, so as to minimize the shear to which the dentifrice ingredients are subjected to during the prior mixing steps.

Initially, the combined composition comprises low solubility flavorant-free polymer matrix film in the dentifrice base that comprises low solubility flavorant. Over time, the low solubility flavorant transfers from the dentifrice base into the polymer matrix films.

In some embodiments, the film matrix is rupturable during tooth brushing so that one or more additives such as the low solubility flavorant is released when the dentifrice is applied topically to tooth surfaces, the mechanical agitation created during tooth brushing effecting rupture of the film matrix whereby the entrained ingredient is released to the tooth surface. In some embodiments, the complete release is extended such that the flavor experience continues after the oral care procedure is performed.

Specific Embodiments

The invention is further described in the following example. The example is merely illustrative and does not in any way limit the scope of the invention as described and claimed.

The film material hydroxypropyl methylcellulose polymer (commercial name—Methocel from Dow Chemical Co.) forms water soluble film. The polymer ethyl cellulose (commercially called Ethocel also made by Dow Chemical Co.) was evaluated for use in polymer matrix films as a low solubility polymer. Ethocel which is widely used in many pharmaceutical and specialty applications as binders, fillers, granulation aids, protective and controlled release coatings, taste masks and flavor fixatives. It is a water insoluble polymer and is used to make water insoluble film Due to process concern emulsified Ethocel material called Surelease E-7-1930 (emulsified Ethocel, containing 25% solid from Colocon Co.) was used to making polymer film.

This technology approach provides the same benefits as those realized when unflavored films are used with toothpaste base comprising menthol which results in unflavored films becoming flavored due to reverse migration that occurs whereby flavor from the toothpaste base migrates to the polymer matrix film. The instant technology further provides the additional benefits of producing product that provide a stronger on intense cooling/taste sensation and having lower formula cost.

The compositions of film slurries made are listed in Table 1.

TABLE 1

| Ingredient | Control film slurry (%) | polymer film A Slurry (%) | polymer film B Slurry (%) | polymer film C Slurry (%) |
|---|---|---|---|---|
| DI Water | 73.17 | 64.17 | 55.17 | 46.17 |
| Methocel E5 | 21.00 | 18.00 | 15.00 | 12.00 |
| Surelease E-7-1930 | — | 12.00 | 24.00 | 36.00 |
| Saccharin | 1.00 | 1.00 | 1.00 | 1.00 |
| Propylene Glycol | 4.00 | 4.00 | 4.00 | 4.00 |
| Colorant | 0.03 | 0.03 | 0.03 | 0.03 |
| Tween 80 | 0.80 | 0.80 | 0.80 | 0.80 |
| Total | 100.00 | 100.00 | 100.00 | 100.00 |

The compositions of dried film are shown in Table 2.

TABLE 2

| Ingredient | Control film (%) | polymer film A (%) | polymer film B (%) | polymer film C (%) |
|---|---|---|---|---|
| Water | 2.00 | 2.00 | 2.00 | 2.00 |
| Methocel E5 | 76.71 | 65.75 | 54.79 | 43.83 |
| Ethocel S4 | — | 10.96 | 21.92 | 32.88 |
| Saccharin | 3.65 | 3.65 | 3.65 | 3.65 |
| Propylene Glycol | 14.61 | 14.61 | 14.61 | 14.61 |
| Colorant | 0.11 $TiO_2$ | 0.11 Red 30 | 0.11 Blue 15 | 0.11 Yellow CL 128 |
| Tween 80 | 2.92 | 2.92 | 2.92 | 2.92 |
| Total | 100.00 | 100.00 | 100.00 | 100.00 |

The colorants, Titanium Dioxide, Red 30, Blue 15 and Yellow CL128 were used to make Control, A, B and C films, respectively. Correspondingly, control film was designated white, film A was designated red, film B was designated blue and film C was designated yellow.

The composition of toothpaste base is listed in Table 3.

TABLE 3

| Ingredient | Toothpaste with Plain Film (%) |
|---|---|
| Polyethylene Glycol 600 | 1.00 |
| CMC 500T | 0.55 |
| Sodium Saccharin | 0.35 |
| Sodium Fluoride | 0.32 |
| Sorbitol (70% solution) | 68.00 |
| Purified Water | 9.05 |
| D&C Red No. 30 | 0.01 |
| Silica Zeodent 114 | 8.00 |

TABLE 3-continued

| Ingredient | Toothpaste with Plain Film (%) |
|---|---|
| Silica Zeodent 165 | 8.00 |
| Cocaamidopropyl Betaine | 1.25 |
| Sodium Lauryl Sulfate | 1.57 |
| Film | — |
| Flavor | — |
| Total | 98.10 |

All test films were performed using circular discs each having a diameter of 0.25 inches. The discs were cut from a larger film using a punch. Discs with the weight of 0.005+/−0.0005 grams/piece were selected for use in the study. Twenty four pieces of each film were used.

Iralia was selected as a model flavor ingredient for the study. Base toothpaste and Iralia were mixed at the ratio of 98.1/1.4. The homogeneity of Iralia in the toothpaste base was checked by HPLC before adding test film discs. Test toothpaste was made by mixing Iralia toothpaste with film discs at the ratio of 99.5/0.5.

After two weeks aging at room temperature four discs of each test film were isolated from aged toothpaste. The toothpaste was removed from each disc by using a spatula first. Remaining residual toothpaste on each disc surface was rubbed off four times using a clean tissue. Each piece of cleaned disc was dissolved by adding 10 ml of Acetonitrate/Water (80/20) in a 20 ml vial. The level of Iralia in the solution was determined by HPLC. The average obtained from four pieces isolated discs are summarized in Table 4.

TABLE 4

| Test Film | Iralia Concentration in film |
|---|---|
| Control - 0% Ethocel white film | 1.46% |
| 11% Ethocel red film A | 4.73% |
| 22% Ethocel blue film B | 12.13% |
| 33% Ethocel yellow film C | 14.18% |

The results indicated that the Ethocel polymer film can significantly enhance flavor reverse migration. The enhancement improves with increasing Ethocel level in the polymer film.

In order to evaluate the dissolution of the films two pieces of each red, blue and yellow disc were soaked in 10 ml deionized water and then the vials were shaken manually. The results showed that the red film (66% Methocell/11% Ethocel) was completely dissociated and water turned red; blue film (55% Methocel/22% Ethocel) and yellow film (44% Methocell/33% Ethocel) did not dissociate.

What is claimed is:

1. A method of preparing a dentifrice comprising a polymer matrix film with a low solubility flavorant therein comprising the steps of:
    a) forming a polymer matrix film in the substantial absence of a low solubility flavorant; wherein said polymer matrix comprises a water soluble polymer and a low solubility polymer additive;
    b) forming a dentifrice base comprising a low solubility flavorant;
    c) combining the polymer matrix film with the dentifrice base; and
    d) maintaining the combined polymer matrix film and dentifrice base for an amount of time suitable for an effective amount of said low solubility flavorant to transfer from said dentifrice base to said polymer matrix film;

wherein the low solubility flavorant is selected from the group consisting of: menthol, spearmint oil, cinnamon oil, peppermint oil, clove oil, bay oil, thyme oil, cedar leaf oil, oil of nutmeg, oil of sage, and oil of bitter almonds, said water soluble polymer comprises hydroxypropyl methyl cellulose and the low solubility polymer additive is ethyl cellulose; and the combined water soluble polymer and low solubility polymer additive makes up by weight between 40-90% of polymer film matrix and the ratio of water soluble polymer to low solubility polymer additive by weight is between 5:2 and 4:3: wherein the polymer matrix film is formed in the substantial absence of alcohol.

2. The method of claim 1 wherein the polymer matrix film further comprises zinc oxide.

3. The method of claim 1 wherein the polymer matrix film further comprises one or more additional components selected from the group consisting of: diols, surfactants, starches, colorants, dyes, sweeteners, whitening agents, breath freshening agents, abrasives, cationic prophylactic and therapeutic agents, fluoride ion sources, stannous ion sources, tartar control agents, antimicrobial agents, antioxidants, saliva stimulating agents, antiplaque agents, anti-inflammatory agents, H2 antagonists, desensitizing agents, nutrients, and proteins; and the dentifrice base further comprises one or more additional components selected from the group consisting of: diols, surfactants, starches, colorants, dyes, sweeteners, whitening agents, breath freshening agents, abrasives, cationic prophylactic and therapeutic agents, fluoride ion sources, stannous ion sources, tartar control agents, antimicrobial agents, antioxidants, saliva stimulating agents, antiplaque agents, anti-inflammatory agents, H2 antagonists, desensitizing agents, nutrients, and proteins.

4. The method of claim 1 further comprising the steps of:
    forming a low solubility flavorant-free polymer matrix film by forming a slurry comprising one or more polymers and free of a low solubility flavorant,
    dispensing the slurry on a surface wherein the slurry forms a layer of slurry on the surface, and
    drying the layer of slurry to produce the low solubility flavorant-free polymer matrix film.

5. The method of claim 4 further comprising the step of after drying the slurry layer to form the low solubility flavorant-free polymer matrix film, cutting or punching the low solubility flavorant-free polymer matrix film to form film flakes or strips of low solubility flavorant-free polymer matrix film prior to combining the film with the dentifrice base.

6. The method of claim 1 wherein the polymer matrix film that is formed comprises hydroxypropyl methylcellulose, ethylcellulose, propylene glycol and polyethylene glycol sorbitan monooleate.

7. The method of claim 6 wherein the dentifrice base that is formed comprises: Polyethylene Glycol 600, carboxymethylcellulose, Sodium Saccharin, Sodium Fluoride, Sorbitol, Purified Water, D&C Red No. 30, silica, cocamidopropyl betaine, Sodium Lauryl Sulfate and Menthol.

8. The method of claim 1 wherein the combined polymer matrix film and dentifrice base comprises 0.2% menthol.

9. The method of claim 1 wherein the combined polymer matrix film and dentifrice base comprises 1% polymer matrix film.

10. A dentifrice product made by the process of claim 1.

11. The method of claim 1, wherein the flavorant is selected from the group consisting of menthol, spearmint oil, cinnamon oil and peppermint oil.

12. The method of claim 2, wherein the flavorant is selected from the group consisting of menthol, spearmint oil, cinnamon oil and peppermint oil.

\* \* \* \* \*